United States Patent [19]
Smith et al.

[11] Patent Number: 5,596,079
[45] Date of Patent: Jan. 21, 1997

[54] MIMETICS OF SENESCENT CELL DERIVED INHIBITORS OF DNA SYNTHESIS

[76] Inventors: James R. Smith, 10311 Cliffwood, Houston, Tex. 77035; Brian K. Kay, 18 Wysteria Way, Chapel Hill, N.C. 27514

[21] Appl. No.: 249,371

[22] Filed: May 24, 1994

Related U.S. Application Data

[63] Continuation-in-part of Ser. No. 229,420, Apr. 15, 1994, which is a continuation-in-part of Ser. No. 203,535, Feb. 25, 1994, abandoned, which is a continuation-in-part of Ser. No. 153,564, Nov. 17, 1993, abandoned, which is a continuation-in-part of Ser. No. 113,372, Aug. 30, 1993, abandoned, which is a continuation-in-part of Ser. No. 970,462, Nov. 2, 1992, Pat. No. 5,302,706, and a division of Ser. No. 160,814, Dec. 3, 1993, Pat. No. 5,424,400, which is a continuation-in-part of Ser. No. 808,523, Dec. 16, 1991, abandoned.

[51] Int. Cl.$^6$ ..................................................... C07K 7/00
[52] U.S. Cl. ........................................... 530/328; 530/300
[58] Field of Search .................................... 530/300, 328; 435/69.1

[56] References Cited

U.S. PATENT DOCUMENTS 5,449,755  9/1995  Roberts et al. ......................... 530/350

FOREIGN PATENT DOCUMENTS

| | | |
|---|---|---|
| 0293249A1 | 5/1988 | European Pat. Off. . |
| WO92/20796 | 11/1992 | WIPO . |
| WO93/06123 | 4/1993 | WIPO . |
| WO93/10242 | 5/1993 | WIPO . |
| WO93/19091 | 9/1993 | WIPO . |
| WO94/09135 | 4/1994 | WIPO . |

OTHER PUBLICATIONS

Drescher–Lincoln, C. K. et al., "Inhibition of DNA Synthesis in Proliferating Human Diploid Fibroblasts by Fusion with Senescent Cells," *Exp. Cell Res.* 144:455–462 (1983).

Drescher–Lincoln, C. K. et al., "Inhibition of DNA Synthesis in Senescent–Proliferating Human Cybrids is Mediated by Endogenous Proteins," *Exp. Cell Res.* 153:208–217 (1984).

Lumpkin, C. K. et al., "Existence of High Abundance Antiproliferative mRNA's in Senescent Human Diploid Fibroblasts," *Science* 232:393–395 (1986).

West, M. D. et al., "Replicative Senescence of Human Skin Fibroblasts Correlates with a Loss of Regulation and Overexpression of Collagenase Activity," *Exp. Cell Res.* 184:138–147 (1989).

Giordano, T. et al., "Identification of a Highly Abundant cDNA Isolated from Senecent WI–38 Cells," *Exp. Cell Res.* 185:399–406 (1989).

Sierra, F. et al., "T–Kininogen Gene Expression Is Induced during Aging," *Molec. Cell. Biol.* 9:5610–5616 (1989).

Maier, J. A. M. et al., "Extension of the Life–Span of Human Endothelial Cells by an Interleukin–1s Antisense Oligomer," *Science* 249:1570–1574 (1981).

Smith, J. R., "A Hypothesis for in vitro Cellular Senescence Based on the Population Dynamics of Human Diploid Fibroblasts and Somatic Cell Hybrids," In:*Monographs in Developmental Biology*; Sauer, H. W. (Ed.), S. Karger, New York, N.Y. 17:193–207 (1984).

Smith, J. R. et al., "Future Studies on the Genetic and Biochemical Basis of Cellular Senescence," *Exper. Gerontol.* 24:377–381 (1989).

Spierling, A. L. et al., "A Potent DNA Synthesis Inhibitor Expressed by the Immortal Cell Line SUSM–1," *Exper. Cell Res.* 179:159–167 (1988).

Pereira–Smith, O. M. et al., "Senescent and Quiescent Cell Inhibitors of DNA Synthesis Membrane–Associated Proteins," *Exper. Cell Res.* 160:297–306 (1985).

Kleinsek, D. A., "Selection of mRNAs Expressed During Cellular Senescence In Vitro," *Age* 12:55–60 (1989).

Pereira–Smith, O. M. et al., "Negative Growth Control in Cellular Senescence, " *J. Cell. Biochem.* (Suppl 0 (12 part A) ,193 (1988).

Kleinsek, D. A. et al., "Isolation of cDNA Sequences Specific to Senescent Human Diploid Fibroblast Cells In Vitro", *Age* 10:125(1987).

Spiering, A. L. et al., "Correlation between Complementation Group for Immortality and DNA Synthesis Inhibitors," *Exper. Cell Res.* 195:541–545 (1991).

Murano, S. et al., "Diverse Gene Sequences Are Overexpressed in Werner Syndrome Fibroblasts Undergoing Premature Replicative Senescence, " *Molec. Cell. Biol.* 11:3905–3914 (Aug. 1991).

Pereira–Smith, O. M. et al., "Genetic Analysis of Infinite Division in Human Cells: Identification of Four Complementation Groups, " *Proc. Natl. Acad. Sci. (U.S.A.)* 85:6042–6046 (1988).

Ning, Y, et al., "Genetic Analysis of Indefinite Division in Human Cells: Evidence for a Cell Senescence–Related Gene(s) on Human Chromosome 4," *Proc. Natl. Acad. Sci. (U.S.A.)* 88:5635–5639 (1991).

Smith, J. R., "Expression of Antiproliferative Genes in Senescent Cells," *J.A.G.S.* 35:894(1987).

Smith, J. R. et al., "Negative Growth Control in Cellular Sensecence," *J. Cell Biochem Suppl.* (13 part C) 147 (1989).

Spiering, A. L. et al., "DNA Synthesis Inhibitors and Their Possible Roles in the Senescence Phenotype, " *J. Cell Biochem Supp. (13 part C)* 166 (1989).

Takebe, Y. et al., "SRa Promoter: An Efficient and Versatile Mammalian cDNA Expression System Composed of the Simian Virus 40 Early Promoter and the R–U5 Segment of Human T–Cell Leukemia Virus Type 1 Long Terminal Repeat," *Mol. Cell. Biol.* 8:466–472 (1988).

Xiong, H. et al., "D Type Cyclins Associate with Multiple Protein Kinases and the DNA Replication and Repair Factor PCNA," *Cell* 71:505–514 (1992).

Sherr, C. J., "Mammalian G1 Cyclins," *Cell* 73:1059–1065 (1993).

Lew, D. J. et al., "Isolation of Three Novel Human Cyclins by Rescue of G1 Cyclin (Cln) Function in Yeast," *Cell* 66:1197–1206 (1991).

Hunter, T. et al., "Cyclins and Cancer," *Cell* 66:1071–1074 (1991).

Norbury, C. et al., "Animal Cell Cycles and Their Controls," *Ann. Rev. Biochem.* 61:441–470 (1992).

Koff, A. et al., "Human Cyclin E, a New Cyclin That Interacts With Two Members of the CDC2 Gene Family," *Cell* 66:1217–1228 (1991).

El–Deiry, W. S. et al., "WAF1, A Potent Mediator of p53 Tumor Suppression," *Cell* 75:817–825 (1993).

Harper, J. W. et al., "The p21 Cdk–Interacting Protein Cip Is A Potent Inhibitor of G1 Cyclin–Dependent Kinases," *Cell* 75:805–816 (1993).

*Primary Examiner*—Garnette D. Draper
*Assistant Examiner*—Stephen Gucker
*Attorney, Agent, or Firm*—Gerard P. Norton

[57] ABSTRACT

Phage display methods were used to identify mimetics of SDI-1. Such mimetics are small peptides that are capable of binding to cyclin molecules, especially CDK2. The invention is directed to the mimetics and to methods for producing them.

1 Claim, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 52 amino acids
( B ) TYPE: amino acid
( D ) TOPOLOGY: lincar ( i i ) MOLECULE TYPE: pcptidc ( i i i ) HYPOTHETICAL: NO ( i v ) ANTI-SENSE: NO ( v ) FRAGMENT TYPE: intcrnal ( v i ) ORIGINAL SOURCE:
( A ) ORGANISM: HOMO SAPIENS ( v i i ) IMMEDIATE SOURCE:
( B ) CLONE: SDI-1 RESIDUES 34- 85

( x i ) SEQUENCE DESCRIPTION: SEQ ID NO:1:

```
Cys Asp Ala Lcu Mct Ala Gly Cys Ilc Gln Glu Ala Arg Glu Arg Trp
1               5                   10                  15

Asn Phc Asp Phc Val Thr Glu Thr Pro Lcu Glu Gly Asp Phc Ala Trp
            20                  25                  30

Glu Arg Val Arg Gly Lcu Gly Lcu Pro Lys Lcu Tyr Lcu Pro Thr Gly
        35                  40                  45

Pro Arg Arg Gly
    50
```

( 2 ) INFORMATION FOR SEQ ID NO:2:

( i ) SEQUENCE CHARACTERISTICS:
( A ) LENGTH: 52 amino acids
( B ) TYPE: amino acid
( D ) TOPOLOGY: lincar ( i i ) MOLECULE TYPE: pcptidc ( i i i ) HYPOTHETICAL: NO ( i v ) ANTI-SENSE: NO ( v ) FRAGMENT TYPE: intcrnal ( v i ) ORIGINAL SOURCE:

(A) ORGANISM: HOMO SAPIENS (vii) IMMEDIATE SOURCE:
(B) CLONE: P16 RESIDUES 48-99

(xi) SEQUENCE DESCRIPTION: SEQ ID NO:2:

Ser Ala Arg Val Ala Glu Leu Leu Leu His Gly Ala Glu Pro Asn
1               5                   10                  15

Cys Ala Asp Pro Ala Thr Leu Thr Arg Pro Val His Asp Ala Ala Arg
            20                  25                  30

Glu Gly Phe Leu Asp Thr Leu Val Val Leu His Arg Ala Gly Ala Arg
        35                  40                  45

Leu Asp Val Arg
    50

(2) INFORMATION FOR SEQ ID NO:3:

(i) SEQUENCE CHARACTERISTICS:
(A) LENGTH: 20 amino acids
(B) TYPE: amino acid
(D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
(A) ORGANISM: HOMO SAPIENS (vii) IMMEDIATE SOURCE:
(B) CLONE: SDI-1 MIMETIC (xi) SEQUENCE DESCRIPTION: SEQ ID NO:3:

Glu Xaa Xaa Xaa Xaa Asp Xaa Xaa Thr Xaa Thr Xaa Xaa Xaa Xaa Asp
1               5                   10                  15

Xaa Ala Xaa Glu
        20

(2) INFORMATION FOR SEQ ID NO:4:

(i) SEQUENCE CHARACTERISTICS:
(A) LENGTH: 6 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
(B) CLONE: recombinant fd phage (xi) SEQUENCE DESCRIPTION: SEQ ID NO:4:

Ser Ser His Gly His Gly
1               5

(2) INFORMATION FOR SEQ ID NO:5:

(i) SEQUENCE CHARACTERISTICS:
(A) LENGTH: 4 amino acids
(B) TYPE: amino acid
(D) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: recombinant fd phage ( x i ) SEQUENCE DESCRIPTION: SEQ ID NO:5:

Cys Gly Ser Arg
1

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: recombinant fd phage ( x i ) SEQUENCE DESCRIPTION: SEQ ID NO:6:

Gly His Gly His Ser Arg
1                5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: recombinant fd phage ( x i ) SEQUENCE DESCRIPTION: SEQ ID NO:7:

Trp Ser Val Gly Asn Trp Glu Ile
1                5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vii) IMMEDIATE SOURCE:
    (B) CLONE: recombinant fd phage (xi) SEQUENCE DESCRIPTION: SEQ ID NO:8:

Pro Gly Gly Ala His Thr Ser Leu
1               5

(2) INFORMATION FOR SEQ ID NO:9:

(i) SEQUENCE CHARACTERISTICS:
       (A) LENGTH: 8 amino acids
       (B) TYPE: amino acid
       (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
       (B) CLONE: recombinant fd phage (xi) SEQUENCE DESCRIPTION: SEQ ID NO:9:

Arg Thr Lys His Gly Glu Val Gly
1               5

(2) INFORMATION FOR SEQ ID NO:10:

(i) SEQUENCE CHARACTERISTICS:
       (A) LENGTH: 8 amino acids
       (B) TYPE: amino acid
       (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
       (B) CLONE: recombinant fd phage (xi) SEQUENCE DESCRIPTION: SEQ ID NO:10:

Met Arg Gly Gln Val Thr Asn Gly
1               5

(2) INFORMATION FOR SEQ ID NO:11:

(i) SEQUENCE CHARACTERISTICS:
       (A) LENGTH: 8 amino acids
       (B) TYPE: amino acid
       (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
       (B) CLONE: recombinant fd phage (xi) SEQUENCE DESCRIPTION: SEQ ID NO:11:

Trp Pro Lys Met Gly Arg Asn Glu
1               5

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: recombinant fd phage (xi) SEQUENCE DESCRIPTION: SEQ ID NO:12:

Pro Ser Gly Thr Thr Val Gly Pro
    1                 5

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: recombinant fd phage (xi) SEQUENCE DESCRIPTION: SEQ ID NO:13:

Gln Gly Pro Leu Asn Thr Lys Arg
    1                 5

MIMETICS OF SENESCENT CELL DERIVED INHIBITORS OF DNA SYNTHESIS

CROSS-REFERENCE TO RELATED APPLICATIONS

This application is a continuation-in-part of U.S. patent application Ser. No. 08/229,420 (filed Apr. 15, 1994), which is a continuation-in-part of U.S. patent application Ser. No. 08/203,535 (filed Feb. 25, 1994) now abandoned, which is a continuation-in-part of U.S. patent application Ser. No. 08/153,564 (filed Nov. 17, 1993) now abandoned, which is a continuation-in-part of U.S. patent application Ser. No. 08/113,372 (filed Aug. 30, 1993) now abandoned, which is a continuation-in-part of U.S. patent application Ser. No. 07/970,462 (filed Nov. 2, 1992, and issued as U.S. Pat. No. 5,302,706 on Apr. 12, 1994); and divisional application Ser. No. 08/160,814 (filed Dec. 3, 1993, now Pat. No. 5,424,400); all of which applications are continuations-in-part of U.S. patent application Ser. No. 07/808,523 (filed Dec. 16, 1991, now abandoned).

FIELD OF THE INVENTION

The present invention is in the field of recombinant DNA technology. This invention is directed to a gene sequence and a protein that effects the ability of cells to become senescent. This invention was supported with Government funds. The Government has certain rights in this invention.

BACKGROUND OF THE INVENTION

Normal human diploid cells have a finite potential for proliferative growth (Hayflick, L. et al., *Exp. Cell Res.* 25:585 (1961); Hayflick, L., *Exp. Cell Res.* 37:614 (1965)). Indeed, under controlled conditions in vitro cultured human cells can maximally proliferate only to about 80 cumulative population doublings. The proliferative potential of such cells has been found to be a function of the number of cumulative population doublings which the cell has undergone (Hayflick, L. et al., *Exp. Cell Res.* 25:585 (1961); Hayflick, L. et al., *Exp. Cell Res.* 37: 614 (1985)). This potential is also inversely proportional to the in vivo age of the cell donor (Martin, G. M. et al., *Lab. Invest.* 23:86 (1979); Goldstein, S. et al., *Proc. Natl. Acad. Sci. (U.S.A.)* 64:155 (1969); Schneider, E. L., *Proc. Natl. Acad. Sci. (U.S.A.)* 73:3584 (1976); LeGuilty, Y. et al., *Gereontologia* 19:303 (1973)).

Cells that have exhausted their potential for proliferative growth are said to have undergone "senescence." Cellular senescence in vitro is exhibited by morphological changes and is accompanied by the failure of a cell to respond to exogenous growth factors. Cellular senescence, thus, represents a loss of the proliferative potential of the cell. Although a variety of theories have been proposed to explain the phenomenon of cellular senescence in vitro, experimental evidence suggests that the age-dependent loss of proliferative potential may be the function of a genetic program (Orgel, L. E., *Proc. Natl. Acad. Sci. (U.S.A.)* 49:517 (1963); De Mars, R. et al., *Human Genet.* 16:87 (1972); M. Buchwald, *Mutat Res.* 44:401 (1977); Martin, G. M. et al., *Amer. J. Pathol.* 74:137 (1974); Smith, J. R. et al., *Mech. Age. Dev.* 13:387 (1980); Kirkwood, T. B. L. et al., *Theor. Biol.* 53:481 (1975).

Cell fusion studies with human fibroblasts in vitro have demonstrated that the quiescent phenotype of cellular senescence is dominant over the proliferative phenotype (Pereira-Smith, O. M. et al., *Somat. Cell Genet.* 8:731 (1982); Norwood, T. H. et al., *Proc. Natl. Acad. Sci. (U.S.A.)* 71:223 (1974); Stein, G. H. et al., *Exp. Cell Res.* 130:155 (1979)).

Insight into the phenomenon of senescence has been gained from studies in which senescent and young (i.e. non-senescent) cells have been fused to form heterodikaryons. In order to induce senescence in the "young" nucleus of the heterodikaryon (as determined by an inhibition in the synthesis of DNA), protein synthesis must occur in the senescent cell prior to fusion (Burmer, G. C. et al., *J. Cell. Biol.* 94:187 (1982); Drescher-Lincoln, C. K. et al., *Exp. Cell Res.* 144:455 (1983); Burner, G. C. et al., *Exp. Cell Res.* 145:708 (1983); Drescher-Lincoln, C. K. et al., *Exp. Cell Res.* 153:208 (1984).

Likewise, microinjection of senescent fibroblast mRNA into young fibroblasts has been found to inhibit the ability of the young cells to synthesize DNA (Lumpkin, C. K. et al., *Science* 232:393 (1986)). Researchers have identified unique mRNAs that are amplified in senescent cells in vitro (West, M. D. et al., *Exp. Cell Res.* 184:138 (1989); Giordano, T. et al., *Exp. Cell Res.* 185:399 (1989)).

The human diploid endothelial cell presents an alternative cell type for the study of cellular senescence because such cells mimic cellular senescence in vitro (Maciag, T. et al., *J. Cell. Biol.* 91:420 (1981); Gordon, P. B. et al., *In Vitro* 19:661 (1983); Johnson, A. et al., *Mech Age. Dev.* 18:1 (1982); Thornton, S. C. et al., *Science* 222:623 (1983); Van Hinsbergh, V. W. M. et al., *Eur. J. Cell Biol.* 42:101 (1986); Nichols, W. W. et al., *J. Cell. Physiol.* 132:453 (1987)).

In addition, the human endothelial cell is capable of expressing a variety of functional and reversible phenotypes. The endothelial cell exhibits several quiescent and non-terminal differentiation phenotypes (Folkman, J. et al., *Nature* 288:551 (1980); Maciag, T. et al., *J. Cell Biol.* 94:511 (1982); Madri. J. A. et al., *J. Cell Biol.* 97:153 (1983); Montesano, R., *J. Cell Biol.* 99:1706 (1984); Montesano, R. et al., *J. Cell Physiol.* 34:460 (1988)).

It has been suggested that the pathway of human cell differentiation in vitro involves the induction of cellular quiescence mediated by cytokines that inhibit growth factor-induced endothelial cell proliferation in vitro (Jay, M. et al., *Science* 228:882 (1985); Madri, J. A. et al., *In Vitro* 23:387 (1987); Kubota, Y. et al., *J. Cell Biol.* 107:1589 (1988); Ingber, D. E. et al., *J. Cell Biol.* 107:317 (1989)).

Inhibitors of endothelial cell proliferation also function as regulators of immediate-early transcriptional events induced during the endothelial cell differentiation in vitro, which involves formation of the capillary-like, tubular endothelial cell phenotype (Maciag, T., *In: Imp. Adv. Oncol. (De Vita, V. T. et al., eds., J. B. Lippincott. Philadelphia,* 42 (1990); Goldgaber, D. et al., *Proc. Natl. Acad. Sci. (U.S.A.)* 86:7606 (1990); Hla, T. et al., *Biochem. Biophys. Res. Commun.* 167:637 (1990)). The inhibitors of cell proliferation that include:

1. Interleukin-1a (IL-1a) (Montesano, R. et al., *J. Cell Biol.* 99:1706 (1984); Montesano, R. et al., *J. Cell Physiol.* 122:424 (1985); Maciag, T. et al. (*Science* 249:1570–1574 (1990));
2. Tumor necrosis factor (Frater-Schroder, M. et al., *Proc. Natl. Acad. Sci. (U.S.A.)* 84:5277 (1987); Sato, N. et al., *J. Natl. Cancer Inst.* 76:1113 (1986); Pber, J. P., *Amer. J. Pathol.* 133:426 (1988); Shimada, Y. et al., *J. Cell Physiol.* 142:31 (1990));
3. Transforming growth factor-β (Baird, A. et al., *Biochem. Biophys. Res. Commun.* 138:476 (1986); Mullew, G. et al., *Proc. Natl. Acad. Sci. (U.S.A.)* 84:5600 (1987); Mairi, J. A. et al., *J. Cell Biol.* 106:1375 (1988));

4. Gamma-interferon (Friesel, R. et al., *J. Cell Biol.* 104:689 (1987); Tsuruoka, N. et al., *Biochem. Biophys. Res. Commun.* 155:429 (1988)) and
5. The tumor promoter, phorbol myristic acid (PMA) (Montesano, R. et al., *Cell* 42:469 (1985); Doctrow, S. R. et al., *J. Cell Biol.* 104:679 (1987); Montesano, R. et al., *J. Cell. Physiol.* 130:284 (1987); Hoshi, H. et al., *FASAB J.* 2:2797 (1988)).

The prospect of reversing senescence and restoring the proliferative potential of cells has implications in many fields of endeavor. Many of the diseases of old age are associated with the loss of this potential. Also the tragic disease, progeria, which is characterized by accelerated aging is associated with the loss of proliferative potential of cells. Restoration of this ability would have far-reaching implications for the treatment of this disease, of other age-related disorders, and, of aging per se.

In addition, the restoration of proliferative potential of cultured cells has uses in medicine and in the pharmaceutical industry. The ability to immortalize nontransformed cells can be used to generate an endless supply of certain tissues and also of cellular products.

The significance of cellular senescence has accordingly been appreciated for several years (Smith, J. R., Cellular Aging, In: *Monographs in Developmental Biology*; Sauer, H. W. (Ed.), S. Karger, New York, N.Y. 17:193–208 (1984); Smith, J. R. et al. *Exper. Gerontol.* 24:377–381 (1989), herein incorporated by reference). Researchers have attempted to clone genes relevant to cellular senescence. A correlation between the existence of an inhibitor of DNA synthesis and the phenomenon of cellular senescence has been recognized (Spiering, A. I. et al., *Exper. Cell Res.* 179:159–167 (1988); Pereira-Smith, O. M. et al., *Exper. Cell Res.* 160:297–306 (1985); Drescher-Lincoln, C. K. et al., *Exper. Cell Res.* 153:208–217 (1984); Drescher-Lincoln, C. K. et al, *Exper. Cell Res.* 144:455–462 (1983)). Moreover, the relative abundance of certain senescence-associated RNA molecules has been identified (Lumpkin, C. K. et al., *Science* 232:393–395 (1986)).

Several laboratories have used the "subtraction-differential" screening method to identify cDNA molecules derived from RNA species that are preferentially present in senescent cells (Kleinsek, D. A., *Age* 12:55–60 (1989); Giordano, T. et al., *Exper. Cell. Res.* 185:399–406 (1989); Sierra, F. et al., *Molec. Cell. Biol.* 9:5610–5616 (1989); Pereira-Smith, O. M. et al., *J Cell. Biochem. (Suppl)* 0 (12 part A)) 193 (1988); Kleinsek, D. A., Smith, J. R., *Age* 10:125 (1987)).

In one method, termed "subtraction-differential" screening, a pool of cDNA molecules is created from senescent cells, and then hybridized to cDNA or RNA of growing cells in order to "subtract out" those cDNA molecules that are complementary to nucleic acid molecules present in growing cells. Although useful, for certain purposes, the "subtraction-differential" method suffers from the fact that it is not possible to determine whether a senescence-associated cDNA molecule is associated with the cause of senescence, or is produced as a result of senescence. Indeed, many of the sequences identified in this manner have been found to encode proteins of the extra-cellular matrix. Changes in the expression of such proteins would be unlikely to cause senescence.

SUMMARY OF THE INVENTION

The present invention concerns, in part, the observation that normal human cells exhibit a limited replicative potential in vitro and become senescent after a certain number of divisions. As the cells become senescent, they show several morphological and biochemical changes, such as enlargement of cell size, changes of extracellular matrix components, unresponsiveness to mitogen stimulation and failure to express growth regulated genes.

The present invention identifies an inhibitor of DNA synthesis that is produced in senescent cells. This inhibitor plays a crucial role in the expression of the senescent phenotype. The gene coding for the inhibitor was identified by incorporating a senescent cell cDNA library into a mammalian expression vector. The cDNA library was then transfected into young, cycling cells to identify those library members that suppressed the initiation of DNA synthesis.

Efficient DEAE dextran-mediated transfection enabled the isolation of putative senescent cell derived inhibitor (SDI) sequences in three distinct cDNA clones. The expression of one (SDI-1) increased 20 fold at cellular senescence, whereas that of the others (SDI-2 and SDI-3) remained constant.

In summary, the present invention achieves the cloning of an inhibitor of DNA synthesis using a functional assay. This method may be applied to clone other genes involved in negative regulation of the cell cycle, such as tissue specific differentiation and tumor suppression genes. Using this method, three inhibitor sequences have been cloned. One of these sequences (SDI-1) appears to be closely related to cellular senescence.

In detail, the invention provides a nucleic acid molecule that encodes a mimetic of SDI-1, the mimetic being a protein or polypeptide capable of binding to a cyclin-dependent kinase.

The invention particularly concerns the embodiments wherein the mimetic encoded by the nucleic acid molecule contains an amino acid sequence selected from the group consisting of SEQ ID NO:1, SEQ ID NO:2 and SEQ ID NO:3.

The invention particularly concerns the embodiments wherein the cyclin-dependent kinase is CDK2, and wherein the encoded mimetic contains an amino acid sequence selected from the group consisting of SEQ ID NO:7, SEQ ID NO:8, SEQ ID NO:9, SEQ ID NO:10, SEQ ID NO:11, SEQ ID NO:12 and SEQ ID NO:13.

The invention also concerns a peptide capable of binding to a cyclin-dependent kinase.

The invention particularly concerns the embodiments wherein the peptide mimetic contains an amino acid sequence selected from the group consisting of SEQ ID NO:1, SEQ ID NO:2 and SEQ ID NO:3.

The invention also concerns the embodiments wherein the cyclin-dependent kinase is CDK2, and wherein the peptide mimetic contains an amino acid sequence selected from the group consisting of SEQ ID NO:7, SEQ ID NO:8, SEQ ID NO:9, SEQ ID NO:10, SEQ ID NO:11, SEQ ID NO:12 and SEQ ID NO:13.

DETAILED DESCRIPTION OF THE INVENTION

I. Cellular Senescence

Replicative senescence of normal human diploid fibroblasts in culture is a well established and widely accepted model for cellular aging (Hayflick, L., *Exp. Cell Res.* 37:611–636 (1965); Norwood, T. H., and Smith, J. R., In: *Handbook of the Biology of Aging* (2nd ed.) C. E. Finch and E. L. Schneider, eds. Van Nostrand, New York pp. 291–311 (1985); Goldstein, S., *Science* 249:1129–1133 (1990)). After a limited number of population doublings, as cells become senescent, they lose the capability to divide and display a large and flattened morphology. The causative mechanisms underlying this phenomenon are not yet understood, despite the many observations that characterize senescent cells at the biochemical and molecular levels.

One- and two-dimensional protein gel analyses have revealed that there are few senescent cell-specific marker proteins (Lincoln, D. W. et al., *Exp. Cell Res.* 154:136–146 (1984); Wang, E., *J. Cell Biol.* 100:545–551 (1985); Scottie, J. et al., *J. Cell Physiol.* 131:210–217 (1987); Bayreuther, K. et al., *Proc. Natl. Acad. Sci. USA.* 85:5112–5116 (1988)). Antigenic determinants that specify senescent cells have been found on the plasma membrane (Porter, M. B. et al., *J. Cell Physiol.* 142:425–433 (1990)). Components of extracellular matrix, such as fibronectin and collagenase, have been found to be over-expressed in senescent cells (West, M. D. et al., *Exp. Cell Res.* 184:138–147 (1989); Kumazaki, T. et al., *Exp. Cell Res.* 195:13–19 (1991)). However, the relevance of these observations to cellular senescence is not clear.

The cell cycle has been found to be regulated and driven by growth factors. Growth factors act throughout the first gap ($G_1$) phase of the cell cycle by binding to specific cell surface receptors, which in turn trigger signaling cascades that ultimately govern the transcription of both immediate and delayed early response genes. The growth cycle is controlled by kinases, especially "cyclin-dependent kinases" ("CDKs"), by the "cyclins" themselves, and by phosphatases (Sherr, C. J., *Cell* 73:1059–1065 (1993), herein incorporated by reference).

Considerable effort has been expended to identify the mammalian kinases that are involved in the DNA synthesis cycle. In vertebrate cells, a family of cyclins has been identified (see, Xiong, H. et al., *Cell* 71:505–514 (1992)). Gene sequences encoding several of these cyclins have been isolated (Motokura, T. et al., *Nature* 350:512–515 (1991); Xiong, H. et al., *Cell* 65:691–699 (1991); Lew, D. J. et al., *Cell* 65:1197–1206 (1991); Xiong, H. et al., *Curr. Biol.* 1:362–364 (1991); Matsushime, H. et al., *Cell* 65:701–7139 (1991); Inaba, T. et al., *Genomics* 13:565–574 (1992); Xiong, H. et al., *Genomics* 13:575–584 (1992)).

The D cyclins interact with CDK2, CDK4 and with CDK5, in order to initiate the growth cycle at the $G_1$ stage (Matsushime, H. et al., *Cell* 65:701–7139 (1991); Sherr, C. J., *Cell* 73:1059–1065 (1993)). Cyclin E/CDK2 interactions regulate the initiation of S phase (Lew, D. J. et al., *Cell* 66:1197–1206 (1991); Koff, A. et al., *Cell* 66:1217–1228 (1991)). Cyclin A has been suggested to interact with CDK2 to regulate the S phase of the growth cycle (Sherr, C. J., *Cell* 73:1059–1065 (1993)). Cyclins A and B are believed to interact with CDC2 to mediate termination of S phase and initiation of $G_2$ phase (Norbury, C. et al., *Ann. Rev. Biochem.* 61:441–470 (1992); Fang, F. et al., *Cell* 66:731–742 (1991); Walker, D. H. et al., *Nature* 354:314–317 (1991)).

Recently, changes in the expression of several growth regulated genes have been identified. Expression of c-fos, CDC2, cyclins A and B have been found to be impaired in senescent cells (Seshadri, T. et al., *Science* 247:205–209 (1990)). Similarly, senescent cells evidence an inability to phosphorylate the retinoblastoma protein (Stein, G. H. et al., *Science* 249:666–669 (1990)). These observations could potentially explain the inability of the cells to enter S phase, since they are all deteriorative changes of growth promoting gene expression, however, it is not clear whether they are the cause or result of senescence.

One additional change in gene expression that could have a causal role in senescence is the inhibitor(s) of DNA synthesis produced by senescent but not young fibroblasts (see, Spiering, A. I. et al., *Exper. Cell Res.* 195:541–545 (1991). Evidence for the existence of the inhibitor(s) was first obtained from heterokaryon experiments in which senescent cells inhibited initiation of DNA synthesis in young nuclei within the heterokaryon (Norwood, T. H., et al., *Proc. Natl. Acad. Sci. USA.* 71:2231–2234 (1974); Pereira-Smith, O. M., and Smith, J. R., *Somat. Cell Genet.* 8:731–742 (1982)). Studies with cybrids involving senescent cytoplasts and whole young cells lent further support for the presence of a surface membrane associated protein inhibitor of DNA synthesis in senescent cells (Dresher-Lincoln, C. K., and Smith, J. R., *Exp. Cell Res.* 153:208–217 (1984)). This was directly demonstrated when surface membrane enriched preparations from senescent cells or proteins extracted from the membranes were found to inhibit DNA synthesis when added to the culture medium of young cells (Pereira-Smith, O. M. et al., *Exp. Cell Res.* 160:297–306 (1985); Stein, G. H., and Atkins, L., *Proc. Natl. Acad. Sci. USA.* 83:9030–9034 (1986)). Purification of that inhibitor by biochemical methods has been unsuccessful to date. However, in microinjection experiments, the presence of a high abundance of DNA synthesis inhibitory messenger RNA has been demonstrated (Lumpkin, C. K. et al., *Science* 232:393–395 (1986)).

In order to attempt to clone the gene(s) coding for the DNA synthesis inhibitor(s), a functional screening procedure was employed. This method led to the isolation and identification of three cDNA species that exhibit DNA synthesis inhibitory activity when introduced into young cycling cells. These molecules are a preferred class of the molecules referred to herein as "senescent cell derived inhibitors" ("SDI molecules").

Subsequent to the cloning, isolation, sequencing and characterization of the SDI molecules of the present invention (see, for example PCT Application Publication No. US93/12251), other research groups conducted similar efforts. Such subsequent efforts have described the SDI-1 molecule of the present invention as WAF1, CIP1, PIC1 and p21 (Harper, J. W. et al., *Cell* 75:805–816 (1993); El-Deiry, W. S. et al., *Cell* 75:817–825 (1993); Xiong, Y. et al., *Nature* 366:701–704 (1993); Hunter, T. et al., *Cell* 75:839–841 (1993)).

II. The Cloning of Inducers of Cellular Senescence

In the practice of the present invention, an efficient method for the molecular cloning of the DNA synthesis inhibitory sequences present in senescent human diploid fibroblasts is preferably employed. As is often the case when attempting to clone biologically important genes, it may not be possible to purify a desired gene responsible for cellular senescence, even though the activity of its products could be readily detected.

One method that might be envisioned for identifying such a gene sequence would be to employ a differential or subtractive screening of a senescent cell derived cDNA library. This method has been used to identify cDNA molecules that are overexpressed in cells from Werner Syndrome patients (Murano, S. et al., *Molec. Cell. Biol.* 11:3905–3914 (August 1991)). Werner Syndrome is a rare inherited disorder. It is characterized by premature aging. The relevance of Werner Syndrome to natural aging is unknown.

Unfortunately, such screenings would identify a number of genes that, although important for the characterization of senescent cells, would not be primarily responsible for senescence. Furthermore, technical limitations in cloning full-length cDNA make it difficult to determine the function of genes cloned by these methods. For these reasons, such differential methods are neither generally suitable, or the most desirable method of identifying senescence-related gene sequences.

In contrast, expression screening provides a preferred method for identifying and isolating such senescence-related gene sequences. In such a screening method, the cDNA is cloned directly into a vector that is capable of expressing the cloned gene in a recipient cell. The recipient cells can thus be directly screened for any inhibition in DNA synthesis.

In expression screening, the most important step is the synthesis of cDNAs. Enzymes should be carefully chosen to be free of impurities. The cDNA synthesis is preferably repeated several times to ensure that satisfactory results (i.e faithful reverse transcription, and full length transcript size) will be obtained. Finally, the cDNA products are preferably size fractionated to eliminate fragmented and prematurely terminated cDNA products. Double-stranded cDNA products are then preferably divided into fractions based on size, i.e., 0.5–2.0, 2.0–4.5, and 4.5–10 kb fractions. The 2–4.5 kb cDNA fraction was used to make the cDNA library on the assumption that many membrane associated proteins have a relatively high molecular weight. The cDNAs are inserted into a suitable expression vector, preferably pcDSRαΔ, in which the inserted sequences can be transcribed at high levels in young cells.

The most preferred transfection procedure is DEAE dextran-mediated transfection, carried out under conditions that allow for transient expression in a high percentage of young cycling cells. Since the transfection frequencies could vary from experiment to experiment, the cDNA pool plasmids were transfected along with a marker plasmid, such as pCMVβ (encoding β-galactosidase), and the labeling index was assayed in only β-galactosidase positive cells. Generally, co-expression of transfected genes is quite high, since transfection competent cells will accept multiple plasmids. This simple co-transfection method enabled the evaluation of DNA synthesis in cells expressing exogenous DNA.

The amount of plasmid to be co-transfected can be readily determined from pilot experiments. When the correlation between the transfection frequency and the amount of plasmid added is examined using a marker plasmid, maximum efficiency is obtained at a range of 100–500 ng of plasmid. Taking into account this result, the cDNA library is preferably divided into small pools in which every pool contained five independent plasmid clones. Then the co-transfection is carried out with approximately 100 ng of pCMVβ and approximately 400 ng of cDNA plasmid. These parameters were found to maximize the co-expression of cDNA in β-galactosidase positive cells without decreasing the transfection frequency of the marker plasmid.

After the second round of screening, single plasmids which showed strong inhibition of DNA synthesis can be successfully isolated from the pool that tested positive during the first round screenings. The inhibitory activities of the plasmids are preferably further confirmed by nuclear microinjection experiments. Such experiments provide more direct evidence that the isolated plasmids contain sequences capable of inhibiting DNA synthesis.

III. The Molecules of the Present Invention

The agents of the present invention are capable of either inducing the inhibition of DNA synthesis in active cells, or suppressing such inhibition in senescent or quiescent cells. As such, they may be used for a wide range of therapies and applications.

As indicated above, the present invention concerns mimetics of the SDI molecules. Such molecules may be either nucleic acids, proteins, carbohydrates, or, more preferably, organic molecules that have a tertiary structure which resembles or mimics the structure of a SDI protein molecule. The present invention further concerns the use of biologically active fragments of molecules, such as SDI nucleic acid molecules, SDI protein molecules, etc. in lieu of or in addition to any naturally occurring SDI molecule. As used herein, a molecule is said to be "biologically active" with respect to cellular proliferation if it is capable of mediating an affect on the proliferative capacity of a recipient cell. Such biological activity may be a structural attribute, such as the capacity to mediate antisense repression, or the ability to bind at a particular nucleic acid site, or with a particular active site of a protein, receptor, etc. (or to compete with another molecule for such binding) Alternatively, such an attribute may be catalytic, and involve the capacity of the biologically active molecule to mediate a chemical reaction or response in a recipient cell.

The present invention permits the isolation of all such SDI mimetics in a "purified" form. As used herein, an SDI mimetic is said to be "purified" if it is present in a preparation that lacks a molecule that is normally associated with the SDI mimetic in its natural state. Proteins, lipids, nucleic acid sequences that do not encode SDI mimetics are examples of molecules that are naturally associated with SDI mimetics.

Nucleic acid mimetics may be obtained using solid phase oligonucleotide synthetic methods, however, more preferably, such molecules will be obtained via the polymerase-mediated, template-dependent extension of a primer molecule that is complementary to a fragment of an SDI nucleic acid molecule. Such fragments of SDI nucleic acid molecules will have a length of between about 15 to about 250 nucleotides, and most preferably about 15 to about 30 nucleotides. Such fragments may be DNA or RNA, and may be incorporated into vectors, or be substantially free of other nucleic acid molecules.

The present invention also pertains to "functional analogs" of the SDI molecules. Such analogs include both "classical analogs" and "mimetic analogs." A classical analog of an SDI molecule is one that has a similar biological activity, and is chemically related to the SDI molecule. By way of illustration, a non-naturally occurring mutant protein having SDI activity would comprise a classical analog of a protein SDI molecule. Similarly, a mutated SDI nucleic acid molecule would comprise an example of a classical analog of an SDI gene sequence. In contrast, a "mimetic analog" of an SDI molecule retains the biological activity of the molecule, but will typically be unrelated chemically. An organic molecule whose structure mimics the active site of an SDI protein would comprise a "mimetic analog" of that protein. Similarly, non-nucleic acid molecules capable of binding to a nucleic acid binding site of SDI, or recognized by SDI would be a mimetic analog of that molecule.

Thus, functional analogs may be either an oligonucleotide or polynucleotide, a proteinaceous compound (including both glycosylated and non-glycosylated proteins), or a non-proteinaceous compound (such as asteroid, a glycolipid, etc.) provided that the agent mimics the function of either an entire SDI nucleic acid molecule, or an oligonucleotide or polynucleotide fragment thereof, or a protein or polypeptide encoded by such a molecule or fragment. Preferred classical analogs include polypeptides (including circular as well as linear peptides) whose sequences comprise the active catalytic or binding sites of an SDI protein, or oligonucleotide fragments of nucleic acid SDI molecules that are capable of either repressing or inducing SDI activity. Preferred mimetic analogs include polypeptides that are not fragments of an SDI protein, or mutants thereof, but nevertheless exhibit a capacity to induce quiescence in an SDl-like manner, or to induce cellular proliferation in the manner of an SDI antagonist.

Classical analogs can be identified either rationally, as described below, or via established methods of mutagenesis (see, for example, Watson, J. D. et al., *Molecular Biology of the Gene*, Fourth Edition, Benjamin/Cummings, Menlo Park, Calif. (1987). Significantly, a random mutagenesis approach requires no a priori information about the gene sequence that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. *Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 8 7:1079–1105 (1987)). Alternatively, where a particular sequence alteration is desired, methods of site-directed mutagenesis can be employed. Thus, such methods may be used to selectively alter only those amino acids of the protein that are believed to be important (Craik, C. S., *Science* 228:291–297 (1985); Cronin, C. S. et al., *Biochem.* 27:4572–4579 (1988); Wilks, H. M. et al., *Science* 242:1541–1544 (1988)).

Nucleic acid analogs of SDI molecules can be evaluated by their capacity to be regulated by p53, or other cellular regulators. Alternatively, their capacity to affect cellular proliferation can be directly assayed. For protein analogs of SDI such studies can be accomplished by purifying the mutant protein, and comparing its activity to an SDI molecule.

The identification of mimetics can also be facilitated through the use of a phage display protein ligand screening system (Lowman, H. B. et al., *Biochem.* 30:10832–10838 (1991); Markland, W. et al., *Gene* 109:13–19 (1991); Roberts, B. L. et al., *Proc. Natl. Acad. Sci. (U.S.A.)* 89:2429–2433 (1992); Smith, G. P., *Science* 228:1315–1317 (1985); Smith, R. P. et al.,*Science* 248:1126–1128 (1990), all herein incorporated by reference)). In general, this method involves expressing a fusion protein in which the desired protein ligand is fused to the N-terminus of a viral coat protein (such as the M13 Gene III coat protein, or a lambda coat protein).

In one embodiment, a library of phage that have been engineered to display novel peptides within their coat protein sequences are placed in contact, with a molecule, such as CDK2, with which SDI-1 binds. Phage that display coat protein having peptides that are capable of binding to such molecules are immobilized by such treatment, whereas all other phage can be washed away. After the removal of unbound phage, the bound phage can be amplified, and the DNA encoding their coat proteins can be sequenced. In this manner, the amino acid sequence of the embedded peptide can be deduced.

If desired, such screens can be modified in order to enhance the probability of identifying mimetics that are competitive inhibitors of SDI-1 (i.e., that bind to the SDI-1 binding site of a cyclin or other molecule that binds SDI-1). In one such screen, phage that bind to CDK2 are identified, and amplified. The phages are then incubated in the presence of both CDK2 and SDI-1. Phage that bind CDK2 at sites other than the SDI-1 binding site will adsorb to the immobilized CDK2. In contrast, phage that bind to the SDI-1 binding site of CDK2 will experience competition for such sites, and will not become immobilized. The CDK2 peptide may be radiolabeled to facilitate the detection of CDK2 molecules that are released by the phage, and which then bind SDI-1. The identified phage may then be recovered, amplified, and analyzed to determine the sequence of the mimetic peptide embedded within their coat proteins.

Mimetic analogs of naturally occurring SDI molecules may also be obtained using the principles of conventional or of rational drug design (Andrews, P. R. et al., In: *Proceedings of the Alfred Benzon Symposium*, volume 28, pp. 145–165, Munksgaard, Copenhagen (1990); McPherson, A. *Eur. J. Biochem.* 189:1–24 (1990); Hol, W. G. J. et al., In: *Molecular Recognition: Chemical and Biochemical Problems*, Roberts, S. M. (ed.); *Royal Society of Chemistry;* pp. 84–93 (1989); Hol, W. G. J., *Arzneim-Forsch.* 39:1016–1018 (1989); Hol, W. G. J., *Agnew Chem. Int. Ed. Engl.* 25:767–778 (1986) all herein incorporated by reference).

In accordance with the methods of conventional drug design, the desired mimetic molecules are obtained by randomly testing molecules whose structures have an attribute in common with the structure of a "native" SDI molecule, or a molecule that interacts th an SDI molecule. The quantitative contribution that results from a change in a particular group of a binding molecule can be determined by measuring the capacity of competition or cooperativity between the native SDI molecule and the putative mimetic.

In one embodiment of rational drug design, the mimetic is designed to share an attribute of the most stable three-dimensional conformation of an SDI molecule. Thus, the mimetic analog of a SDI molecule may be designed to possess chemical groups that are oriented in a way sufficient to cause ionic, hydrophobic, or van der Waals interactions that are similar to those exhibited by the SDI molecule. In a second method of rational design, the capacity of a particular SDI molecule to undergo conformational "breathing" is exploited. Such "breathing"—the transient and reversible assumption of a different molecular conformation—is a well appreciated phenomenon, and results from temperature, thermodynamic factors, and from the catalytic activity of the molecule. Knowledge of the 3-dimensional structure of the SDI molecule facilitates such an evaluation. An evaluation of the natural conformational changes of an SDI molecule facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the SDI molecule could assume, and enables the rational design and production of mimetic analogs that share such conformations.

The preferred method for performing rational mimetic design employs a computer system capable of forming a representation of the three-dimensional structure of the SDI molecule (such as those obtained using RIBBON (Priestle, J., *J. Mol. Graphics* 21:572 (1988)), QUANTA (Polygen), InSite (Biosyn), or Nanovision (American Chemical Society). Such analyses are exemplified by Hol, W. G. J. et al. (In: *Molecular Recognition: Chemical and Biochemical Problems*, Roberts, S. M. (ed.); Royal Society of Chemistry; pp. 84–93 (1989)), Hol, W. G. J. (*Arzneim-Forsch.* 39:1016–1018 (1989)), and Hol, W. G. J., *Agnew Chem. Int. Ed. Engl.* 25:767–778 (1986)).

In lieu of such direct comparative evaluations of putative SDI analogs, screening assays may be used to identify such molecules. Such an assay will preferably exploit the capacity of the SDI analog to affect cellular proliferation or quiescence. Alternatively, the molecules may be applied to a column containing a binding ligand, such as p53, Rb, cyclin D, etc., and the capacity of the molecule to bind to the column may be evaluated in comparison to the SDI molecule. Alternatively, a mutated SDI molecule (that inhibits the SDI-mediated inhibition of DNA synthesis) can be administered with a suspected antagonist compound. The cells would in this case be monitored to determine whether the compound is able to re-establish an inhibition of DNA synthesis.

Such assays are particularly useful for identifying peptide or oligonucleotide fragments of SDI molecules, or analogs of such molecules. Thus, for example, one may incubate cells in the presence of either an oligonucleotide or a peptide SDI analog (or fragment) and a suspected antagonist compound. The cells would be monitored in order to determine whether the compound is able to impair the ability of the SDI oligonucleotide to inhibit DNA synthesis. As indicated above, column competition assays could alternatively be conducted. Thus, desired SDI classical and mimetic analogs may be identified by a variety of means.

Significantly, an appreciation of the mechanisms through which SDI molecules mediate their inhibition of DNA synthesis provides an alternative, or complimentary, approach to the isolation and recognition of analogs.

As indicated above, cyclin-dependent kinases play an important role in controlling the process of cellular DNA synthesis (Draetta, G. et al., *Trends Biol. Sci.* 5:378–383 (1990)). The SDI molecules of the present invention may be used to dissect the role of such kinases, and the involvement of such cyclins, and to thereby identify SDI analogs that can be used to inhibit DNA synthesis. For example, the D-type cyclins are believed to play a role in the G1 or S phase of DNA synthesis (Xiong, H. et al., *Cell* 71:505–514 (1992)). The level of cyclin D protein increases throughout G1, declines during S and G2, and reaches a nadir after mitosis (Matsushime, H. et al., *Cell* 65:701–7139 (1991); Klyokawa, H. et al., *Proc. Natl. Acad. Sci. (U.S.A.)* 89:2444–2447 (1992); Xiong, H. et al., *Cell* 71:505–514 (1992)).

Xiong, H. et al. (*Cell* 71:505–514 (1992)) reported the existence of a 21 kd polypeptide that associates with cyclin D1 and CDK2. An immunological precipitation method was used in which radiolabelled extracts of cells were incubated in the presence of anti-cyclin antibodies. Proteins that associated with these antibodies were subjected to electrophoresis, and visualized.

The sequence of this 21 kd polypeptide has now been determined, and found to be encoded by SDI-1. Thus, since SDI-1 encoded molecules inhibit DNA synthesis, the present invention establishes a biological role for the 21 kd protein. Moreover, since the SDI-1 encoded protein interacts with cyclin D1 and CDK2, the present invention establishes that agents that inhibit or reduce this interaction will be analogs of the SDI molecules. Recently, a novel tumor suppressor molecule, designated p16, has been described (Kamb, A. et al., *Science* 264:436 (1994)). Significantly, although p 16 and SDI-1 share slight homology, the homology centers about a region (amino acids 34–85 of SDI-1 (SEQ ID NO:1) and amino acids 48–99 of p16 (SEQ ID NO:2)) that is important to the biological function of SDI-1. SDI-1 deletion proteins that lack this region exhibit severely attenuated activity. Thus, a peptide having the sequence of amino acids 34–85 of SDI-1 (SEQ ID NO:1) or of amino acids 48–99 of p16 (SEQ ID NO:2) comprise mimetic inhibitors of SDI-1 activity. More preferred inhibitors will have the sequence of amino acids 47–66 of SDI-1 (residues 14–33 SEQ ID NO:1) or of amino acids 61–80 of p16 (SEQ ID NO:2). The most preferred of such mimetics will have a sequence EXXXXDXXTXTXXXXDXAXE (SEQ ID NO:3), or a subsequence of SEQ ID NO:3, wherein X is any amino acid, and E, D, T and A designate glutamate, aspartate, threonine and alanine, respectively.

The immunological precipitation method used by Xiong, H. et al. (*Cell* 71:505–514 (1992)) to demonstrate the association of the 21 kd polypeptide and the cyclin D1 and CDK2 molecules may be exploited to determine the mechanism or pathway through which other SDI molecules mediate their inhibitory effect, and thereby permit the identification of other analogs.

Thus, the recognition that SDI molecules exert their control over cellular proliferation through interactions with cylins and CDK molecules provides an alternate approach to the identification of SDI analogs. In a similar manner, the recognition that other cellular regulators mediate their actions by regulating SDI transcription or expression provides yet another alternate method for identifying SDI analogs.

For example, the transcription of the SDI-1 gene has been found to be regulated by "tumor suppressor" genes, and most notably by the p53 tumor suppressor gene. Indeed, the "tumor suppressor" capacity of p53 results from its capacity to induce SDI-1 expression, and thereby induce cellular quiescence in tumor cells.

The p53 gene has been previously found to encode a tumor-suppressing protein (Sager, R., *Science* 246:1406–1412 (1989); Finlay, C., *Cell* 57:1083 (1989); Weinberg, R. A., *Scientific Amer.*, September 1988, pp 44–51); Lane, D. et al. (*Genes Devel.* 4:1–8 (1990)). The p53 gene has also been found to play a protective role against the transforming effects of Friend erythroleukemia virus (Munroe, D. et al. *Oncogene* 2:621 (1988)), and to influence chromosome stability, differentiation and quiescence, and cell proliferation (Sager, R., *Science* 246:1406–1412 (1989)). It has been found that wild type p53 is necessary for cell cycle arrest following ionizing radiation and the constitutive expression of wild type p53 can arrest mammalian cells in G1. The ability to induce cell cycle arrest is thought to be related to p53's tumor suppressor function. The protein encoded by the p53 gene is a nuclear protein that forms a stable complex with both the SV40 large T antigen and the adenovirus E1B 55 kd protein.

Approximately 50% of all tumor cells evidence a mutation that diminishes or obliterates p53 expression. The p53 gene has been implicated as having a role in colorectal carcinoma (Baker, S. J. et al., *Science* 244:217–221 (1989)). Studies have shown that allelic deletions that encompass the p53 locus occurred in over 75% of colorectal carcinomas (Baker, S. J. et al., *Science* 244:217–221 (1989)). The deletion of the region was found to mark a transition from a (benign) adenocarcinoma stage to a (malignant) carcinomatous stage (Vogelstein, B. et al., *New Engl. J. Med.* 39:525 (1988)).

Similar deletions in chromosome 17 have been identified in a wide variety of cancers including breast and lung cancers (Mackay, J. et al., *Lancet ii*:1384 (1988); James, C. D. et al., *Canc. Res.* 48:5546 (1988); Yakota, J. et al., *Proc. Nat'l. Acad. Sci. (U.S.A.)* 84:9252 (1987); Toguchida et al., *Canc. Res.* 48:3939 (1988)). A variety of human tumors (brain, colon, breast, lung) are characterized by cells that have lost one of the two normal p53 alleles, and have sustained a point mutation in the remaining p53 allele (Nigro et al., *Nature* 342:705–708 (1989)). Fearon et al. (*Cell*

61:759–767 (1990)) have hypothesized that both point mutations and deletions in the p53 alleles may be required for a fully tumorigenic phenotype. These findings suggest that the p53 gene may have a role in many types of cancers.

Recent evidence has suggested that a mutation in the p53 gene may be responsible for the Li-Fraumeni Syndrome, a rare human genetic disorder (Malkin, D. et al., *Science* 250:1233–1238 (1990); Marx, J., *Science* 250:1209 (1990), both references herein incorporated by reference). Individuals afflicted with this disease are highly susceptible to several malignant tumors—breast carcinomas, soft tissue sarcomas, brain tumors, osteosarcomas, leukemia, and adrenocortical carcinoma. The disease is also associated with a higher incidence of melanoma, gonadal germ cell tumors, and carcinomas of the lung, pancreas and prostate (Li, F. P. et al., *Ann. Intern. Med.* 71:747 (1969); Birch, J. M. et al., *J. Clin. Oncol.* 8:583 (1990); Birch, J. M. et al., *Brit. J. Canc.* 49:325 (1984); Li, F. P. et al., *Canc. Res.* 48:5358 (1988); Williams, W. R. et al., *Familial Canc.*, 1*st Int. Res. Conf.* p. 151 (Karger, Basel, 1985); Strong, L. C. et al., *J. Natl. Canc. Inst.* 79:1213 (1987)).

Despite the extensive prior characterization of the biological role of the p53 gene, the mechanism through which its gene product mediated its tumor suppressor activity had not been previously elucidated. One aspect of the present invention relates to the discovery of that this mechanism involves SDI-1. Normal p53 protein increases the expression of SDI-1, and such increased expression suppresses cellular proliferation. In tumor cells that lack p53 function, SDI-1 levels are quite low, thus permitting cellular proliferation to occur.

The physiological significance of inhibition of cell proliferation by overexpression of SDI-1 is strengthened by the finding that SDI-1 can inhibit the kinase activity of cyclin/cdk2 complexes. Addition of a GST-SDI-1 fusion protein to cyclin/cdk2 complexes immunoprecipitated from HeLa cell extracts by cdk2 antisera resulted in half maximal inhibition of histone H1 kinase activity.

Thus, molecules that inhibit the tumor suppressor activity of p53 are antagonists of SDI-1; similarly, molecules that enhance the tumor suppressor activity of p53 are protagonists of SDI-1, and are also encompassed by the present invention.

The present invention thus also pertains to antagonists of the SDI molecules. Such antagonists may comprise SDI analogs that compete with, or that inhibit SDI function. Alternatively, such antagonists may comprise analogs of molecules such as cell cyclins or p53, that interact with SDI molecules.

Any of a variety of methods can be used to identify polypeptides or non-proteinaceous molecules that inhibit or repress SDI function. Such molecules can be evaluated to determine whether they compete with normal SDI molecules, or whether their presence in a cell affects the capacity of an SDI molecule to induce a quiescent state. For example, nucleic acid molecules that competitively bind p53 molecules are antagonists of SDI molecules. Such competitors can be readily identified using affinity columns, or by DNAse-footprinting methods.

Analogs of p53, or other tumor suppressor proteins, that are capable of interacting with and activating SDI sequences are an additional class of antagonists. Inhibitors of p53 (and other tumor suppressors) are likewise antagonists of the SDI molecules. Such molecules may be obtained by, for example, mutagenizing p53-encoding cDNA, and identifying p53 muteins that retain the capacity to bind to SDI-1 gene sequences or to SDI-1 proteins, but are otherwise inactive. The sequences of the cDNA and genomic forms of the p53 gene have been determined (Pennica, D. et al., *Virol.* 134:477–482 (1984); Jenkins, J. et al., *Nature* 312:651–654 (1984); Oren, M. et al., *EMBO J.* 2:1633–1639 (1983); Zahut-Houri, R. et al., *Nature* 306:594–597 (1983), all of which references are herein incorporated by reference).

Alternatively, candidate inhibitors can be provided to a recipient cell and their capacity to impair normal p53 function can be ascertained. For example, such molecules can be tested for their capacity to prevent p53 from forming complexes with the SV40 large T antigen (see, DeCaprio, J. A. et al., *Cell* 54:275–283 (1988); Crawford, L. V., *Int. Rev. Exper. Pathol.* 25:1–50 (1983)).

Similarly, a variety of means can be exploited in order to identify nucleic acid molecules that inhibit or repress SDI-mediated inhibition of DNA synthesis. For example, the SDI nucleic acid sequences can be mutated, and the mutated sequences provided to cells in order to identify cells that do not exhibit an inhibition of DNA synthesis, and which have therefore received the desired mutated SDI sequences. In yet another method, the SDI gene sequences of immortalized cell lines can be evaluated to determine whether they contain mutated SDI genes that have lost the capacity to mediate cellular quiescence. In such manner, it has been determined that some immortalized cells (approximately 10%) carry a mutation in the SDI-1 gene that results in the substitution of arginine at amino acid residue 31 of SDI-1 (in place of the serine residue normally found at this position). Such a finding also implicates residue 31 of SDI-1 as being relevant to the active site or conformation of SDI-1. Since DNA from 12 normal Caucasian donors did not have this SDI-1 substitution, it is believed that the $Arg_{31}$ SDI-1 variant reflects mutation rather than a polymorphism.

Other mutant SDI proteins have been identified by screening the SDI proteins of various cell lines. Thus, for example, SDI-1 mutants have been identified in which the valine normally found at amino acid residue 54 has been replaced with alanine, or in which the threonine normally found at amino acid residue 80 has been replaced with methionine. Table 1 shows the observed correlation between SDI-1 mutations and their incidence in cancer cells and cell lines.

TABLE 1

| | Observed Changes | | |
|---|---|---|---|
| Sample Type | Codon 31 AGC (ser) → AGA (arg) | Codon 80 ACG (thr) → ATG (met) | Codon 54 GTC (val) → GCC (ala) |
| Normal Individuals | 8/80 (10%) | 0/62 (0%) | 0/62 (0%) |
| Tumor Cell Lines | 9/38 (24%) | 4/38 (11%) | 1/38 (3%) |
| Endometrial | 4/9 (44%) | 4/9 (44%) | 0/9 (0%) |

TABLE 1-continued

| Sample Type | Observed Changes | | |
|---|---|---|---|
| | Codon 31 AGC (ser) → AGA (arg) | Codon 80 ACG (thr) → ATG (met) | Codon 54 GTC (val) → GCC (ala) |
| Cancer Cell Lines | | | |
| Primary Endometrial Cancers | 3/43 (7%) | 0/43 (0%) | 0/43 (0%) |
| Primary Breast Cancers | 7/29 (24%) | 0/29 (0%) | Not Determined |

Alternatively, mutated SDI sequences expressed from such nucleic acid molecules can be evaluated for their capacity to bind p53 protein, or the gene products of other tumor suppressor genes such as rb, etc.

The present invention thus also pertains to protagonists of the SDI molecules. As used herein, a "protagonist" of an SDI molecule is a molecule that enhances or increases the biological activity of an SDI molecule.

Since p53 is an inducer of SDI expression, it, or a nucleic acid encoding p53, or biologically active fragments of either, may be provided to cells in conjunction with an SDI molecule in order to obtain increased SDI expression.

The present invention also provides SDI protagonists other than the naturally occurring tumor suppressor proteins. Such protagonists may comprise SDI analogs or may comprise non-analog molecules that interact with the cellular molecules that interact with SDI molecules. Thus, mutant forms of the p53 protein having enhanced SDI-activating capacity comprise one illustrative SDI protagonist. Such molecules may be produced by mutating the p53 gene, and then selecting muteins that effect more rapid or more extensive induction of SDI-1 activity than the normal p53 protein.

Similarly, SDI protagonists can be identified through the use of screening assays in which, for example, a candidate molecule is provided to a recipient cell along with an SDI molecule, and the capacity of the candidate molecule to enhance SDI expression is monitored. The above-described methods of rational mimetic design can be used to define SDI protagonists.

IV. Uses of the SDI Molecules of the Present Invention and their Inhibitors

A. Induction of Senescense or Quiescence

Molecules capable of inhibiting SDI function, when provided to a recipient cell cause the immortalization of the cell, and thereby permit the establishment of a permanent cell line. The antisense, ribozyme and other SDI inhibitor molecules of the present invention may thus be used to immortalize valuable cell types (such as primary tissue culture cells, etc.) which would otherwise have a transient period of proliferative viability. They may thus be used for research or to permit or facilitate the accumulation of large numbers of cells, as for organ or tissue grafts or transplants. In one embodiment, therefore, the agents of the present invention may be used in conjunction with methods for organ or tissue culture to facilitate such methods. Such molecules may alternatively be used to effect the immortalization of immunoglobulin producing cells, or cells that produce important biologicals, such as hormones (insulin, growth hormone, IGF, etc.), immune system modifiers (such as interferons, adhesion molecules, lymphokines, etc.).

Such inhibitory nucleic acid molecules will preferably have nucleotide sequences that are complementary to the sequences of the SDI molecules, and most preferably will be complementary to the sequence of regions or all of the SDI-1 gene. When such oligo-nucleotides are provided to recipient cells, the immortalization of the cell line occurs. Alternatively, the antibodies of the present invention may be used to inhibit SDI activity (e.g., to prevent SDI in a fluid (such as blood) from mediating the quiescence of cells that are in contact with the fluid).

B. Diagnostic Uses

A major use of the molecules of the present invention lies in their capacity to diagnose the presence and predisposition to cancer. Since the absence of SDI-1 expression is the mechanism through which p53-dependent cancers mediate tumorigenicity, assays of cellular SDI-1 expression can be used to diagnose the presence and severity of human cancers. For example, the Li-Fraumeni Syndrome is associated with a particular set of mutations in exon 7 of the p53 gene (Malkin, D. et al., *Science* 250:1233–1238 (1990), herein incorporated by reference). Cells of Li-Fraumeni patients do not produce detectable SDI-1 mRNA or SDI-1 protein. Thus, a diagnosis of this disease may be made using hybridization assays, or immunoprecipitation protocols that measure SDI-1 mRNA or protein levels.

As indicated, approximately 50% of human tumors fail to express normal p53 protein. Thus, assays for p53 activity in biopsy samples is can be used to assess the presence of tumors. Such assays can be readily accomplished using the SDI molecules of the present invention, especially the SDI-1 gene sequences, and their fragments. Since p53 is an inducer of SDI expression, the detection of SDI-1 molecules or mRNA in a biopsy material is suggestive of the normal expression of the p53 gene.

C. Therapeutic Uses

The molecules of the present invention also posess therapeutic utility. A use is said to be therapeutic if it alters a physiologic condition. A non-therapeutic use is one which alters the appearance of a user. The agents of the present invention may be used topically or systemically for a therapeutic or non-therapeutic purpose, such as, for example, to counter the effects of aging, for example on skin tone, color, texture, etc., or on the degeneration of cells, tissue or organs, such as lymphocytes, vascular tissue (such as arteries, arterioles, capillaries, veins, etc.), liver, kidney, heart and other muscle, bone, spleen, etc. The agents of the present invention may be employed to rejuvenate such cells, tissue or organs. Thus, they may be used in pharmaceuticals, and the like, which may comprise, for example, an antisense oligonucleotide, or its equivalent, and a lipophilic carrier or adjunct, preferably dissolved in an appropriate solvent. Such a solvent may be, for example, a water-ethanol mixture (containing 10% to 30% v/v or more ethanol. Such preparations may contain 000.1% to 1.0% of the antisense oligonucleotide. Suitable carriers, adjuncts and solvents are described in Remington's Pharmaceutical Sciences (16th ed., Osol, A., Ed., Mack, Easton Pa. (1980), which reference is incorporated herein by reference).

1. Treatment of Cancer and Other Diseases

SDI mimetics and analogs have use in inducing a senescent or quiescent state in a recipient cell. Such induction is desirable in the treatment of progeria (Badame, A. J., *Arch. Dermatol.* 125:540 (1989); Hamer, L. et al., *Orthoped.* 11:763 (1988); Martin, G. M., *Natl. Canc. Inst. Monogr.* 60:241 (1982)); age-related disorders (Martin, G. M., *Genome* 31:390 (1989); Roe, D. A., *Clin. Geriatr. Med.* 6:319 (1990); Mooradian, A. D., *J. Amer. Geriat. Soc.* 36:831 (1988); Alpert, J. S., *Amer. J. Cardiol.* 65:23j (1990)); Alzheimer's disease (Terry, R. D., *Monogr. Pathol.* 32:41 (1990); Costall, B. et al., *Pharmacopsychiatry* 23:85 (1990)); asthenia and cachexia (Verdery, R. B., *Geriatrics* 45:26 (1990)), or similar diseases or conditions. In this respect, the agents of the present invention can be used therapeutically to suppress the rapid proliferation of tumor or tumorigenic cells. Thus, in particular, the molecules of the present invention may be used in the treatment of cancer, particularly liver, pancreatic, kidney, lung, stomach, breast, uterine, colon, skin, gliomal, lymphatic, prostate, or hepatobiliary cancer. Indeed, as discussed below, SDI-1 has broad activity in suppressing the proliferation of tumor cells, such as breast, lung, hepatic and glioma tumor lines.

In one embodiment, such treatment is accomplished by providing SDI-1 mimetic to tumor cells. Such mimetic may be provided directly, since SDI-1 appears to be capable of directly entering tumor cells. Alternatively, SDI-1 may be provided in liposomes, viral sheaths, or other vehicles. In a second embodiment, gene sequences that encode SDI-1 or fragments of SDI-1 may be provided as a gene therapy for cancer.

In the case of melanoma or other skin cancers, the SDI molecules of the present invention may be provided topically, in an emollient, etc. (preferably formulated with a UV-adsorbing compound, such as p-aminobenzoic acid (PABA)

The SDI molecules of the present invention may be used alone, or in combination with other conventional chemotherapeutic agents to decrease the effective concentrations that would otherwise be required in order to achieve a therapeutic effect.

2. Antiviral and Antimicrobial Uses

In an alternative embodiment, the molecules of the present invention may by used as an anti-viral agent to impair the propagation of visurses such as influenza, hepatitis (e.g., hepatitis B or hepatitis C), Epstein-Barr, rhinovirus, etc. In particular, since SDI molecules (especially, SDI-1 and its analogs) act to inhibit cellular proliferation, and since retroviruses preferentially proliferate only in actively dividing cells, the present invention provides an antiviral therapy against HIV, and thus can be used to treat diseases such as AIDS and ARC.

In another embodiment, the molecules of the present invention may be used as an anti-parasitic agent to treat fungal, yeast, protozoan, helminthic, nematodal and other parasitic infections (e.g., candidiassis, aspergillosis, coccidiomycosis, leishmaniasis, amoebiasis, trichomoniasis, tinea (pedis, crusis, etc.) vaginal monolysis, schistosomiasis and malaria.

3. Other Therapeutic Uses

The SDI inhibitor molecules of the present invention may be used to stimulate the proliferation of spermatocytes, or the maturation of oocytes in humans or animals, and thus, may be used to increase the fertility of a recipient. Conversely, SDI molecules and their analogs can be used to inhibit gametogenesis in males or females, and thus can be used as contraceptive agents to induce infertility in males or females.

Since the molecules of the present invention are capable of stimulating cellular proliferation, they may be used to promote wound healing, angiogenesis, endothelial cell proliferation, recovery from burns, or after surgery, or to restore atrophied tissue, etc. Indeed, all such compounds can also be used to suppress general tissue regeneration or vascularization. For such an embodiment, these agents may be formulated with antibiotics, anti-fungal agents, or the like, for topical or systemic administration.

The molecules of the present invention may be used to provide gene therapy for recipient patients. In one embodiment, cells or tissue from a patient may be removed from the patient and treated with a molecule of the present invention under conditions sufficient to permit a restoration of an active growing state. In one preferred embodiment of this use, lymphocytes of an individual (such as, for example, an immune compromised individual, such as an AIDS patient, etc., or an immune-competent individual who will serve as a donor of lymphocytes) can be removed and treated with antisense SDI nucleic acids. The administration of these molecules will derepress the lymphocytes. After administration, the lymphocytes are reintroduced into the patient, and have an enhanced ability to combat infection.

In yet another embodiment of the present invention, the molecules of the present invention can be used to facilitate autologous cell replacement. In this embodiment, the SDI nucleic acid molecules, their fragments, encoded proteins and polypeptides, and analogs can be used to permit the in vitro proliferation of cells (such as bone marrow cells, epithelial cells, muscle cells, hepatic cells, etc.) in order to replenish or augment the amount or concentration of such cells in a patient. Thus, for example, bone marrow cells can be removed, treated with such molecules, and then cultured in vitro until a sufficient mass of cells has been obtained to augment a desired immune response. Alternatively, hepatic cells (such as hepatic cells that are free of a hepatitis virus) can be removed from a patient, treated, cultured and then transplanted back into the patient in order to treat hepatic disease.

In one sub-embodiment, such treated cells may be themselves directly transplanted back into the patient, and thus propagate in vivo. Alternatively, as indicated, such cells may be cultured in vitro, and reintroduced when a desired titer has been attained.

The molecules of the present invention are particularly suitable for use in the creation and/or study of animal models for disease or tissue degeneration. Thus, the molecules of the present invention can be used to study effectors of an animal model that is characterized by abnormal aging or cellular degeneration. Similarly, the administration of the SDI molecules (linked, for example to suitable regulatory sequences in order to permit their expression in a recipient cell) can be used to create animal models of aging or of tissue degeneration.

V. Methods of Administration

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of an antisense oligonucleotide, or its equivalent, or their functional derivatives, together with a suitable amount of carrier vehicle.

Additional pharmaceutical methods may be employed to control the duration of action. Control release preparations may be achieved through the use of polymers to complex or absorb an antisense oligonucleotide, or its equivalent, or their functional derivatives. The controlled delivery may be exercised by selecting appropriate macromolecules (for example polyesters, polyamino acids, polyvinyl pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate an antisense oligonucleotide, or its equivalent, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compositions of the present invention can also be formulated for administration parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

Generally, the dosage needed to provide an effective amount of the composition will vary depending upon such factors as the recipient's age, condition, sex, and extent of disease, if any, and other variables which can be adjusted by one of ordinary skill in the art.

Effective amounts of the compositions of the invention can vary from 0.01–1,000 mg/ml per dose or application, although lesser or greater amounts can be used.

Having now generally described the invention, the same will be more readily understood through reference to the following examples which are provided by way of illustration, and are not intended to be limiting of the present invention, unless specified.

EXAMPLE 1

CHARACTERIZATION OF SDI SEQUENCES

Using a functional screening method, a novel DNA synthesis inhibitory gene, SDI-1, was identified (Smith, J. R., U.S. Pat. No. 5,302,706). The gene is expressed at high levels in nonproliferating human diploid fibroblasts. Message levels of SDI-1 increased 10 to 20-fold as normal human cell cultures were aged in vitro, with the expression kinetics correlating closely with the phenotypic expression of cellular senescence. In addition, SDI-1 message increased when cells were made quiescent by growth factor deprivation.

The results described above demonstrate that SDI-1 codes for a novel, physiologically active gene product that is important for cell cycle control. Expression of the gene is modulated during exit from $G_0$ and entry into S phase in cells that have been stimulated to enter the cell cycle. In addition, expression of antisense SDI-1 message stimulates cells to enter the cell cycle in the absence of growth factors. The observation that SV40 T antigen can counteract the inhibitory activity of SDI-1 in a manner similar to that observed with the negative growth regulators p53 and Rb (Harper, J. W. et al., *Cell* 75:805–816 (1993); Lane, D. P. et al., *Nature* 278:261–263 (1979); Linzer, D. I., H. et al., *Cell* 17:43–52 (1979); De Caprio, J. A. et al., *Cell* 54:275–283 (1988)), underscores the importance of this gene product in the regulation of the cell cycle.

The recombinant SDI-1 protein of the present invention inhibits the phosphorylation of histone H1 by CDK2. This activity can be used to determine whether a molecule is an inhibitor or protagonist of SDI-1.

The SDI-1 gene product is also a potent inhibitor of several cyclin-dependent kinases, including CDC2, CDK2, and CDK4. In similar experiments using human cell extracts, recombinant SDI-1 was found to inhibit CDK2 kinase activity. These results are of particular importance in view of what is known about the various proteins involved in cell cycle progression. Several human G1 cyclin candidates (cyclins C, D, and E), identified by their ability to complement a budding yeast strain that lacked G1 cyclins (Xiong, H. et al., *Cell* 65:691–699 (1991); Lew, D. J. et al., *Cell* 65:1197–1206 (1991); Xiong, H. et al., *Curr. Biol.* 1:362–364 (1991); Koff, A. et al., *Cell* 66:1217–1228 (1991)), were found to be cell cycle regulated, with maximal mRNA expression occurring at different points in G1 (Lew, D. J. et al., *Cell* 65:1197–1206 (1991)). Since D-type cyclins and cyclin E are associated with active kinase complexes (Koff, A. et al., *Cell* 66:1217–1228 (1991); 1992; Dulic, V. et al., *Science* 257:1958–1961 (1992); Matsushime, H. et al., *Cell* 65:701–7139 (1991); Ewen, M. E. et al., *Cell* 73:487–4976 (1993); Kato, J. Y. et al., *Genes Devel.* 7:331–342 (1993), it is likely that these kinases have a role in the commitment of mammalian cells to a new round of cell division at the "restriction point." (Pardee, A. B., *Science* 246:603–608 (1989)). Indeed, recent reports indicate that cyclin E-CDK2 kinase complexes have maximal activity in late G1 and early S phase (Dulic, V. et al., *Science* 257:1958–1961 (1992); Koff, A. et al., *Cell* 66:1217–1228 (1991)), and also have the ability to phosphorylate the RB protein in cultured human cells (Hinds, P. W. et al., *Cell* 70:993–1006 (1992)) and in vitro (Ewen, M. E. et al., *Cell* 73:487–4976 (1993)). This suggests that the kinase may play a pivotal role in the regulation of the G 1-to-S phase transition of the cell cycle.

Immunoblots of SDI-1 protein have revealed that levels of this protein do not appear to vary extensively in cells in different growth states (i.e., actively growing versus quiescent or senescent cells). However, consistently higher amounts of protein are present in non-dividing compared with proliferating cells. This seems reasonable because SDI-1 is a potent negative regulator of CDK activity, and tight regulation of this inhibitor would be essential for proper cell cycle regulation and progression. Small changes in the amount of inhibitor protein could result in a major impact on the various gene products it controls. At least two CDKs, CDC2 and CDK2, maintain relatively constant steady-state protein levels through the cell cycle despite cell cycle phase-dependent changes in mRNA. SDI-1 may be regulated in a similar manner, such that the level of SDI-1 protein is precisely controlled at a particular level, and that new CDK/cyclin synthesis and activation is needed to overcome the inhibitory effects of SDI-1 to allow for progression through the cell cycle. Thus, SDI-1 would prevent entry into the cell cycle until a required threshold of stimulatory gene products were present, allowing the cell to proceed through the "restriction point" of the cell cycle. Such a dynamic equilibrium between active CDK/cyclin complexes and the inhibitor SDI-1 protein explains the observed stimulation of DNA synthesis in quiescent cells following a small decrease in the steady-state levels of SDI-1 protein due to antisense SDI-1 mRNA expression. Thus, SDI-1 may function in the cell in a manner similar to other cell proliferation inhibitors, such as the tumor suppressor genes p53 and Rb, and the SDI-1 gene may be a target for mutation in various tumors.

Although senescent cells cannot be stimulated to enter S phase by the addition of mitogens, they do express mRNAs for many cell cycle-regulated genes including cyclins D1, cyclin E, CDK2, Rb, p53, c-H-ras, c-myc, c-jun, and jun B. However, several other important cell cycle-regulated genes, including c-fos, histone H3, CDC2, cyclin A, cyclin B1, and PCNA, are not expressed in mitogen-stimulated senescent cells. The lack of phosphorylation of the protein product of the retinoblastoma susceptibility gene Rb in senescent cells could be one cause for the inability of senescent cells to synthesize DNA. However, cyclin E-CDK2 complexes, though relatively abundant in senescent cells, lack the kinase activity which could potentially phosphorylate Rb in vivo.

The SDI molecules of the present invention are expressed at a higher level in senescent than in actively cycling cells. Thus, lack of proper CDK activity through the regulatory action of SDI-1 could be a key reason for the inability of senescent cells to enter S phase. This is supported by the fact that senescent cells are primarily deficient in events downstream of the postulated SDI-1 mediated inhibition of CDK2.

Overexpression of E2F-1, a component of the E2F-1 transcription factor which has a wide range of target genes, was found to be capable of reversing the inhibitory effect of SDI-1. It is well established that the tumor suppressor gene Rb, as well as the related p107 protein complexes with E2F-1 to inhibit transcription. Overexpression of cyclins A and E reverses pRb-mediated suppression of proliferation. In addition, overexpression of E2F-1 can induce quiescent REF-52 cells to synthesize DNA. Thus, in view of the observation that E2F-1 reverses the negative growth activity of SDI-1, E2F-1 may be the last step in a cascade of events controlled by p53, SDI-1 and Rb.

A role for SDI-1 in cell cycle arrest is indicated by the fact that in normal human cells made quiescent either by serum deprivation or growth to high density, SDI-1 mRNA levels were increased 10–20 fold compared with cycling cells. However, upon addition of serum, SDI-1 mRNA levels were found to rapidly decrease to low levels just prior to the onset of DNA synthesis. Thus SDI-1 appears to act as a "check point" to inhibit cell proliferation in the presence of unfavorable external conditions. Many immortal cell lines are unable to block initiation of DNA synthesis in response to insufficient growth factors. However, in accordance with the present invention, the overexpression of SDI-1 in various immortal human cells resulted in inhibition of DNA synthesis in several of the cell lines regardless of their ability to arrest cell proliferation in response to lowered growth factors.

EXAMPLE 2

CAPACITY OF SDI-1 TO SUPPRESS THE PROLIFERATION OF TUMOR CELLS

As indicated above, SDI-1 has the capacity to suppress the proliferation of tumor cells. To demonstrate this ability, cells derived from several human tumors were incubated in the presence or absence of a glutathione S-transferase-SDl-1 fusion protein. In the experiment, $5 \times 10^3$ cells were plated overnight at 37° C. (only for adherent cells) and then incubated with the SDI fusion protein. After 48 hours at 37° C., cells were pulsed with thymidine for 24 hours and then harvested. The results of this experiment are shown in Table 2; the thymidine incorporation by untreated cells was expressed as 100%. All determinations were made in quadruplicate.

TABLE 2

| Antiproliferative Effects of SDI-1 | | |
|---|---|---|
| | Relative Cell Viability (% of Control) | |
| Cell Line | 50 µg/ml | 30 µg/ml |
| Myeloid Cells: | | |
| Promyelocytic (HL-60) | 1 ± 0 | 1 ± 0 |
| Promonocytic (ML-1) | 1 ± 0 | 1 ± 0 |
| Myelogenous (KG-1) | 1 ± 0 | 1 ± 0 |
| Myelogenous (KG-1a) | 1 ± 0 | 1 ± 0 |
| Histiocytic Lymphoma (U-937) | 1 ± 0 | 1 ± 0 |
| Promonocytic (THP-1) | 1 ± 0 | 1 ± 0 |
| B Cell Lymphoma | | |
| Burkitt Lymphoma (Daudi) | 1 ± 0 | 3 ± 0 |

TABLE 2-continued

Antiproliferative Effects of SDI-1

| Cell Line | Relative Cell Viability (% of Control) | |
|---|---|---|
| | 50 µg/ml | 30 µg/ml |
| Burkitt Lymphoma (Raji) | 1 ± 0 | 1 ± 0 |
| Epithelial Cells | | |
| Breast (BT-20) | 1 ± 0 | 1 ± 0 |
| Breast (BT-20 TNF R) | 1 ± 0 | 1 ± 0 |
| Breast (SK-BR3) | 1 ± 0 | 1 ± 0 |
| Breast (MCF-7) | 1 ± 0 | 1 ± 0 |
| Breast (T-47 D) | 2 ± 0 | 2 ± 0 |
| Lung adenocarcinoma (A-549) | 25 ± 3 | 40 ± 1 |
| Hepatocellular (Hep G2) | 12 ± 2 | 21 ± 3 |
| Glioblastoma Cells | | |
| Glial (U-251) | 35 ± 2 | 66 ± 4 |
| Normal Cells | | |
| Human umbilical vein endothelial cells | 2 ± 1 | 5 ± 1 |
| Human foreskin fibroblasts | 1 ± 0 | Not Done |
| Murine Tumor Cells | | |
| Fibroblasts (L-929) | 4 ± 1 | Not Done |

The above experiment indicates that tumor cells treated with SDI-1 exhibited a profound suppression of DNA synthesis.

EXAMPLE 3

EFFECT OF SDI-1 cDNA ON THE PROLIFERATION OF TUMOR CELLS

The capacity of SDI-1 cDNA to repress the proliferation of tumor cells was evaluated. SDI-1 cDNA was introduced into a number of tumor derived and other cell lines by electroporation. One µg of the CMV-SDI-1 plasmid was mixed with 1 µg of plasmid containing the CMV promoter and the β-galactosidase gene. After electroporation, cells were plated and 24 hours later assayed for the ability to incorporate tritiated thymidine. SDI-1 cDNA caused significant inhibition of DNA synthesis in a number of tumor derived cell lines including a melanoma, lung tumor and a brain tumor. The SDI-1 cDNA also inhibited DNA synthesis in mouse 3T3 cells and in normal bovine smooth muscle cells. Three tumor derived cell lines (one lung tumor cell line, and two kidney tumor cell lines) were unresponsive to the SDI-1 cDNA.

EXAMPLE 4

THE IDENTIFICATION OF SDI-1 MIMETICS

As indicated above, SDI-1 interacts with, and inhibits, cyclins and other molecules (such as CDC2, CDK2 and CDK4) that are involved in cell cycle regulation. The recognition of this attribute of SDI-1 was used to identify mimetics of SDI-1. Such mimetics can be used as competitive inhibitors of SDI-1, or as inhibitors (competitive, non-competitive or uncompetitive) of the cellular ligands of SDI-1 (such as the cyclins, CDCs and CDKs). Moreover, they may be used in the same manner as SDI-1 or antibodies to assay for molecules that interact with SDI-1.

In order to identify such mimetics, the M663 M13 bacteriophage display screening system was employed (Fowlkes, D. M. et al., Biotechniques 13:422–427 (1992)), herein incorporated by reference). The system exploits several fortuitous attributes of the major capsid protein of M13 (i.e., the pIII protein). The pIII protein is expressed on the surface of M13 bacteriophages, and possesses a carboxy terminal portion which is buried within the virion surface, and an amino terminal portion which extends outside the virion, and is thus accessible for binding (in vivo, the pIII protein binds to the F pilus of F+ or Hfr E. coli strains, and thus mediates phage infection) (Pratt, D. et al., Virol. 39:42–53 (1969); Grant, R. A. et al., J. Biol. Chem. 256:539–546 (1981); Scott, J. K., et al., Science 249:386–390 (1990); Parmley, S. F. et al., Gene 73:305–318 (1988)). Significantly, the pIII protein is relatively insensitive to insertions of peptides that precede those pIII domains necessary for pilus attachment.

The M663 M13 vector was been engineered to contain XhoI and XbaI sites within the amino terminal portion of the pIII-encoding gene (Fowlkes, D. M. et al, Biotechniques 13:422–427 (1992)). An oligonucleotide encoding an 11 residue long c-myc epitope is present between these sites. The M663 vector was cleaved with XhoI and XbaI, thereby excising the c-myc epitope. The cleaved molecule was incubated in the presence of a library of oligonucleotides having an XhoI site at one end and an XbaI site at the other. The sequences of these oligonucleotides were selected such that they contained a unique "epitopic" sequence flanked by a set of fixed sequences. The fixed sequences were either:

SSC-epitopic sequence-CGSR
SSHGHG-epitopic sequence-GHGHGSR
SR-epitopic sequence-SR SSHGHG is SEQ ID NO:4; CGSR is SEQ ID NO:5; GHGHSR is SEQ ID NO:6. Fixed sequences having flanking cysteine residues are capable of forming disulfide bonds that create a "closed loop" around the epitopic sequence (O'Neil, K. et al., Proteins 14:509–515 (1992); Felici, F. et al., Gene 128:21–27 (1993); Luzzago, A. et al., Gene 128:51–57 (1993)). Fixed sequences that contain histidine residues have the potential of forming "Zinc finger"-like structures around the epitopic region. The epitopic sequences were prepared using a pseudo-random synthesis in which the first and second bases of each codon were either A,C,T or G, and the third base of each codon was T or G. Each phage of the library thus displays its unique epitopic sequence as part of the larger gene III protein. This epitopic sequence is flanked by preceding ("proximal") sequences and by trailing ("distal") sequences.

Purified CDK2 was allowed to coat a polystyrene microtiter plate. Non-specific adsorption was blocked by the addition of bovine serum albumin. An aliquot of the library was added to the plate and permitted to bind to the immobilized CDK2. The plates were washed to remove non-binding phages, and then subjected to treatment with acid (e.g., 0.1N HCl, 1 mg/ml bovine serum albumin; pH adjusted to 2.2 with glycine) (Parmley, S. F. et al., Gene 73:305–318 (1988)) in order to release bound phages. After such release, the pH of the solution was neutralized, and the bound phages were amplified by permitting them to infect and propagate in E. coli cells. The purification was repeated twice to ensure the separation of non-binding phages.

The DNA sequence of the epitopic region and gene III flanking regions of phages that had bound to CDK2 was determined and the relevant amino acid sequences of the displayed pIII product was deduced. The sequences of 7 different phages that were capable of binding CDK2 are shown in Table 3.

TABLE 3

| SEQ ID NO | Amino Acid Sequence | | |
|---|---|---|---|
| of Epitopic Sequence | Proximal Sequence | Epitopic Sequence | Distal Sequence |
| 7 | SSC | WSVGNWEI | CGSR |
| 8 | SSC | PGGAHTSL | CGSR |
| 9 | SSC | RTKHGEVG | CGSR |
| 10 | SSC | MRGQVTNG | CGSR |
| 11 | SSHGHG | WPKMGRNE | GHGHGSR |
| 12 | SSHGHG | PSGTTVGP | GHGHGSR |
| 13 | SSHGHG | QGPLNTKR | GHGHGSR |

Ten different isolates of bound phage displayed the sequence of SEQ ID NO:7. In sum, the above-described experiment identified molecules which like SDI-1 are capable of binding to CDK2. Such mimetics of SDI-1 have diagnostic and therapeutic utility, as described above.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. The peptide selected from the group consisting of SEQ ID NO:7, SEQ ID NO:8, SEQ ID NO:9, SEQ ID NO:10, SEQ ID NO:11, SEQ ID NO:12 and SEQ ID NO:13.

* * * * *